(12) United States Patent
Slingsby et al.

(10) Patent No.: US 9,074,972 B2
(45) Date of Patent: Jul. 7, 2015

(54) SURROGATE ADDITION DEVICE AND A METHOD OF ANALYTE CONCENTRATION

(75) Inventors: Rosanne Williamson Slingsby, Pleasanton, CA (US); Jing Hong, Cupertino, CA (US); Douglas M. Jamieson, Patterson, CA (US); Christopher A. Pohl, Union City, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 380 days.

(21) Appl. No.: 13/473,318

(22) Filed: May 16, 2012

(65) Prior Publication Data

US 2013/0309777 A1    Nov. 21, 2013

(51) Int. Cl.
   *B01D 21/00*    (2006.01)
   *G01N 1/40*    (2006.01)
   *G01N 33/18*    (2006.01)
   *G01N 30/00*    (2006.01)

(52) U.S. Cl.
   CPC ............... *G01N 1/40* (2013.01); *Y10T 436/255* (2015.01); *Y10T 436/24* (2015.01); *G01N 1/405* (2013.01); *G01N 30/00* (2013.01); *G01N 33/1893* (2013.01)

(58) Field of Classification Search
   None
   See application file for complete search history.

(56) References Cited

U.S. PATENT DOCUMENTS

| | | |
|---|---|---|
| 3,845,770 A | 11/1974 | Theeuwes et al. |
| 4,364,385 A | 12/1982 | Lossef |
| 4,448,691 A | 5/1984 | Davis |
| 4,666,441 A | 5/1987 | Andriola et al. |
| 4,837,161 A | 6/1989 | Stevens et al. |
| 5,458,568 A | 10/1995 | Racchini et al. |
| 6,050,150 A | 4/2000 | Underhill et al. |
| 6,890,372 B2 | 5/2005 | Dasgupta et al. |
| 7,059,206 B1 | 6/2006 | Kingston et al. |
| 7,872,225 B2 | 1/2011 | Whitehouse et al. |

(Continued)

FOREIGN PATENT DOCUMENTS

| | | |
|---|---|---|
| EP | 223763 A1 | 5/1987 |
| EP | 617611 B1 | 5/1994 |

(Continued)

OTHER PUBLICATIONS

Alnouti, Y. et al., Method for Internal Standard Introduction for Quantitative Analysis Using On-Line Solid-Phase Extraction LC-MS/MS, 2006, Analytical Chemistry, vol. 78(4), pp. 1331-1336.*

(Continued)

*Primary Examiner* — Robert Xu
(74) *Attorney, Agent, or Firm* — Timothy J. Ohara

(57) ABSTRACT

A surrogate addition device is described that adds a surrogate compound at a uniform transport rate to a flowing sample stream. The surrogate addition device includes a surrogate reservoir, a flow chamber, and a diffusion barrier. The surrogate reservoir can be configured to contain a surrogate solution where the surrogate solution includes a surrogate compound. The flow chamber includes an inlet port and an outlet port. At least a portion of the diffusion barrier is disposed in between the surrogate reservoir and the flow chamber. The diffusion barrier may include an inner surface that forms a wall of the surrogate reservoir, and an outer surface that forms a wall of the flow chamber. The flow chamber can be configured to receive a flowing sample solution across the outer surface of the diffusion barrier and also to diffuse the surrogate compound from the surrogate reservoir to the flow chamber.

22 Claims, 11 Drawing Sheets

(56) References Cited

U.S. PATENT DOCUMENTS

| | | |
|---|---|---|
| 2003/0096422 A1 | 5/2003 | Ong et al. |
| 2004/0007459 A1 | 1/2004 | Herchen |
| 2009/0084157 A1 | 4/2009 | Krogh et al. |
| 2011/0144585 A1 | 6/2011 | Bianchi et al. |
| 2012/0016311 A1 | 1/2012 | Altman et al. |

FOREIGN PATENT DOCUMENTS

| | | |
|---|---|---|
| EP | 783341 B1 | 7/1997 |
| EP | 869363 B1 | 7/1998 |
| JP | 5788358 A | 6/1982 |
| WO | 2009015238 A1 | 1/2009 |

OTHER PUBLICATIONS

3212 Federal Register, vol. 54, No. 13, Jan. 23, 1989, 18 pages.

Qun and Rohrer, Thermo Fisher Scientific Application Update: 186, Rapid HPLC Determination of Carbofuran and Carbaryl in Tap and Environmental Waters Using On-Line SPE, copyright 2012, 6 pages.

Othmer, Membrane Technology, Wiley-Interscience, 3rd Edition, vol. 15, pp. 92-127, copyright 1984, John Wiley & Sons, NY.

Thurman and Mills, Solid-Phase Extraction—Principles and Practice, vol. 147, John Wiley & Sons, Inc., copyright 1998, pp. 1-23.

J. Camilleri et al., "Determination of the uptake and release rates of multifamilies of endocrine disruptor compounds on the polar C18 Chemcatcher. Three potential performance reference compounds to monitor polar pollutants in surface water by integrative sampling," J. of Chromatography A, vol. 1237, May 1, 2012, pp. 37-45.

Seethapathy et al., "Passive sampling in environmental analysis," J. of Chromatography, Elsevier Science Publishers B.V, NL, vol. 1184, No. 1-2, Feb. 28, 2008, pp. 234-253.

* cited by examiner

US 9,074,972 B2

SURROGATE ADDITION DEVICE AND A METHOD OF ANALYTE CONCENTRATION

BACKGROUND

There is increasing interest in using analytical techniques to monitor chemicals in the environment. For example, herbicides in lakes, rivers, ponds, and reservoirs may be monitored to ensure that the water is safe to drink or that it will not endanger the habitat. In many instances, analytical techniques for water will require a relatively large liquid volume (e.g., 100 mL to 1000 mL of liquid) and the sample location can be far from the analytical laboratory. It should be noted that analytical instrumentation such as, for example, high pressure liquid chromatography (HPLC) and capillary chromatography cannot be easily transported to the sample source because they are relatively heavy and delicate instruments. For these reasons, most procedures for sampling remote bodies of water require the collection and shipment of the water samples from the remote site to the laboratory. In addition to the cost and inconvenience of collecting, bottling, preserving, and shipping the water, there are possibilities for cross-contamination and errors at each step in the process.

In an environmental study, water can be monitored for a prolonged period of time. It may not be convenient or cost-effective to have a human operator perform the water sampling process. One possibility is to use a pump can that is configured to extract water from the sample source at a constant flow for a period of time and stored in a container. An issue with using a pump is that it needs to have sufficient power and a uniform flow rate for the entire sampling period. Applicants believe that there is a need for a device and method that can verify that the sample has been collected properly. In addition, Applicants believe that the verification device and method should not require electrical power so that implementation in a remote setting would be easy to use.

SUMMARY

A surrogate addition device is described that adds a surrogate compound at a uniform transport rate to a flowing sample stream. The surrogate addition device includes a surrogate reservoir, a flow chamber, and a diffusion barrier. The surrogate reservoir can be configured to contain a surrogate solution where the surrogate solution includes a surrogate compound. The flow chamber includes an inlet port and an outlet port. At least a portion of the diffusion barrier is disposed in between the surrogate reservoir and the flow chamber. The diffusion barrier may include an inner surface that forms a wall of the surrogate reservoir, and an outer surface that forms a wall of the flow chamber. The flow chamber can be configured to receive a flowing sample solution across the outer surface of the diffusion barrier and also to diffuse the surrogate compound from the surrogate reservoir to the flow chamber. An axis, running along a direction of a flowing sample solution through the inlet port, forms an angle with respect to a line segment running along a direction of a flowing sample solution from the inlet port to the outlet port. The angle may range from about 100 degrees to about 170 degrees.

In an embodiment, the diffusion barrier may also be configured to have an approximately uniform diffusion rate of the surrogate compound to the flow chamber during a sampling period that includes a time duration in which the sample solution is pumped through the flow chamber to concentrate the analyte on the solid phase extraction device. The diffusion rate of the surrogate compound from the surrogate reservoir to the flow chamber may range from about 4 attomoles per minute to about 100 picomoles per minute at a flow rate of about one milliliter per minute. The approximately uniform diffusion rate may have a relative standard deviation of less than about 5% during the sampling period. The diffusion barrier may also be configured so that there is essentially no bulk flow of sample solution across the diffusion barrier during the sampling period. The flow chamber may include a height that is defined by the outer surface of the diffusion barrier and an opposing wall of the flow chamber where the height ranges from about 0.6 millimeters to about 13 millimeters. The surrogate addition device may be orientated where the outer surface of the diffusion barrier is an approximately planar surface that is approximately parallel to a gravity vector line.

A system for concentrating an analyte from a sample source is described. The system includes a pump, a surrogate addition device, and a solid phase extraction device. The pump can be configured to pump a sample solution from the sample source to a solid phase extraction device. The surrogate addition device can be fluidically coupled to an outlet of the pump. The surrogate reservoir can be configured to contain a surrogate solution where the surrogate solution includes a surrogate compound. The flow chamber includes an inlet port and an outlet port. At least a portion of the diffusion barrier is disposed in between the surrogate reservoir and the flow chamber. The diffusion barrier may include an inner surface that forms a wall of the surrogate reservoir, and an outer surface that forms a wall of the flow chamber. The flow chamber can be configured to receive a flowing sample solution across the outer surface of the diffusion barrier and also to diffuse the surrogate compound from the surrogate reservoir to the flow chamber. The solid phase extraction device can be fluidically coupled to the outlet port of the flow chamber. The solid phase extraction device can be configured to bind the surrogate compound and the analyte from the sample solution.

A method for concentrating an analyte from a sample source includes pumping a sample solution from the sample source to a surrogate addition device. A surrogate compound can be added to the sample solution with the surrogate addition device. The sample solution from the surrogate addition device can be flowed to a solid phase extraction device. The analyte and a surrogate compound can be bound from the sample solution to the solid phase extraction device. As a next step, the analyte and the surrogate compound from the solid phase extraction device can be eluted. The eluted analyte and the eluted surrogate compound can be analyzed with an analytical instrument such as, for example, a liquid chromatograph, a mass spectrometer, a gas chromatograph, an ultraviolet-visible spectrometer, a fluorescence spectrometer, a flame ionization detector, an electrochemical detector, or a combination thereof.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements). A detailed understanding of the features and advantages of the present invention will be obtained by reference to the following detailed description that sets forth illustrative embodiments, in which the principles of the invention are utilized, and the accompanying drawings of which.

DETAILED DESCRIPTION OF EMBODIMENTS

Figure 1:
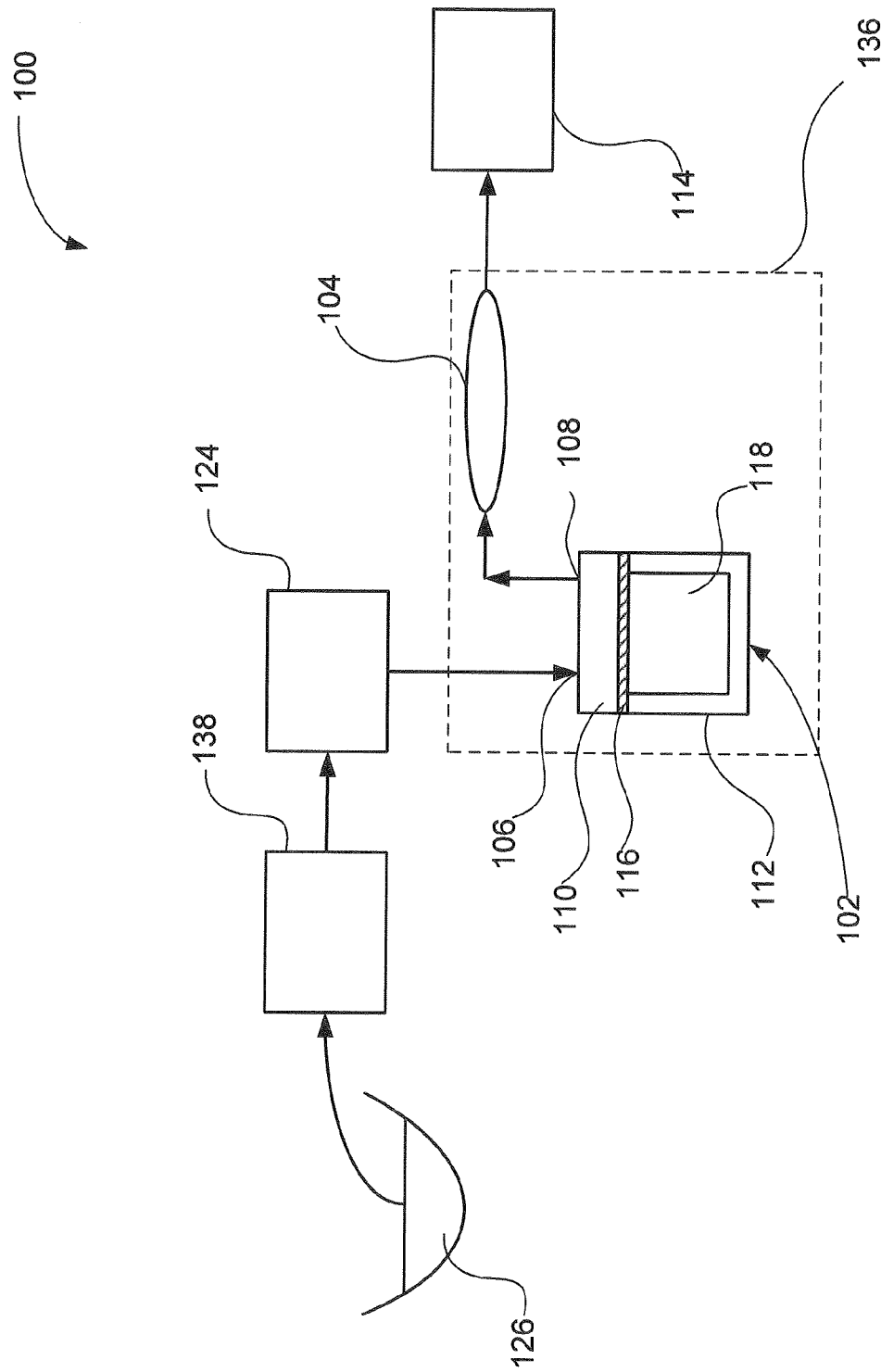
FIG. 1 illustrates a schematic of a system for concentrating an analyte that includes a surrogate addition device and a solid phase extraction device.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

A sample can be collected from a sample source to monitor an analyte. In an embodiment, a pump can be used to collect the sample over a period of time. When monitoring chemicals in water, the concentration of analyte in the sample can be relatively low, and thus, difficult to measure. To circumvent this issue, a solid phase extraction device can be used to concentrate the analyte and at the same time reduce the overall volume of the sample. Binding the analyte to a solid phase extraction device allows the sample to be transported to the laboratory more easily and then subsequently analyzed. A solid phase extraction device is typically a relatively small and light device that can be easily shipped as compared to a one liter bottle of water.

In order to perform a precise and accurate measurement with the solid phase extraction device, the pump should have a uniform flow rate so that the volume of fluid flowing through the solid phase extraction device can be in accordance with a predetermined protocol. However, under certain circumstances, the pump can malfunction and cause the flow rate to be higher or lower that the set amount. A device and method will be described that can determine whether the pump worked properly during the collection of sample. Such a device can be a surrogate addition device that releases a uniform amount of a surrogate compound into a flowing sample stream, which will then be subsequently bound by the solid phase extraction device. Assuming that the pump performed properly at the set flow rate, an amount of surrogate compound that is bound to the solid phase extraction device can be calculated. If the measured amount of surrogate bound to the solid phase extraction device is not within a predetermined range, then a system error can be identified. In an embodiment, a lower limit and upper limit of the predetermined range may be based on a predetermined percentage of the calculated amount of surrogate compound. The predetermined percentage may be about ±20%, preferably be about ±10%, and more preferably be about ±5%.

The system error may be a pump malfunction during the sample collection process. It should be noted that variations in pump flow will cause the amount of analyte and surrogate compound bound to the solid phase extraction device to be elevated or decreased in a false manner. The system error may also be the result of an error in the measurement process. Assuming that there is no error in the collection process, the surrogate compound will act as an internal reference that validates data quality. Errors in the measurement process can affect the measured amount of surrogate compound and thus will also likely affect the measured amount of analyte. Thus, a sufficiently large difference between the predicted amount and the actual measured amount of surrogate compound may also indicate a processing error or contamination with the analytical technique.

FIG. 1 illustrates a schematic of a system 100 for concentrating an analyte that includes a pump 124, a surrogate addition device 102, and a solid phase extraction device 104 (SPE). System 100 may optionally include an insulated housing 136 and an insulated line 138 where external temperatures can influence the sample collection process. Pump 124 can be configured to pump a sample solution from a sample source 126 to surrogate addition device 102. An outlet port 108 of surrogate addition device 102 can be fluidically connected to an inlet of solid phase extraction device 104. An outlet of solid phase extraction device 104 can be fluidically connected to a waste container 114. It should be noted that pump 124 can be in other locations within system 100 so long as the sample flows through both surrogate addition device 102 and then solid phase extraction device 104. Surrogate addition device 102 should be upstream of solid phase extraction device 104 so that the surrogate compound can be bound.

In an embodiment, pump 124 may be a mechanical pump that is battery powered. Alternatively, pump 124 can be powered by solar energy or a combination of solar and battery energy. Sample source 126 can be a liquid sample such as, for example, water. Sample source 126 can be large body of water such as a lake, river, pond, or reservoir. Pump 124 can be configured to pump liquid at a rate of about 0.1 milliliters per minute to about 10 milliliters per minute, preferably range from about 0.2 milliliters per minute to about 8 milliliters per minute, and more preferably range from about 0.5 milliliters per minute to about 2 milliliters per minute.

Figure 2:
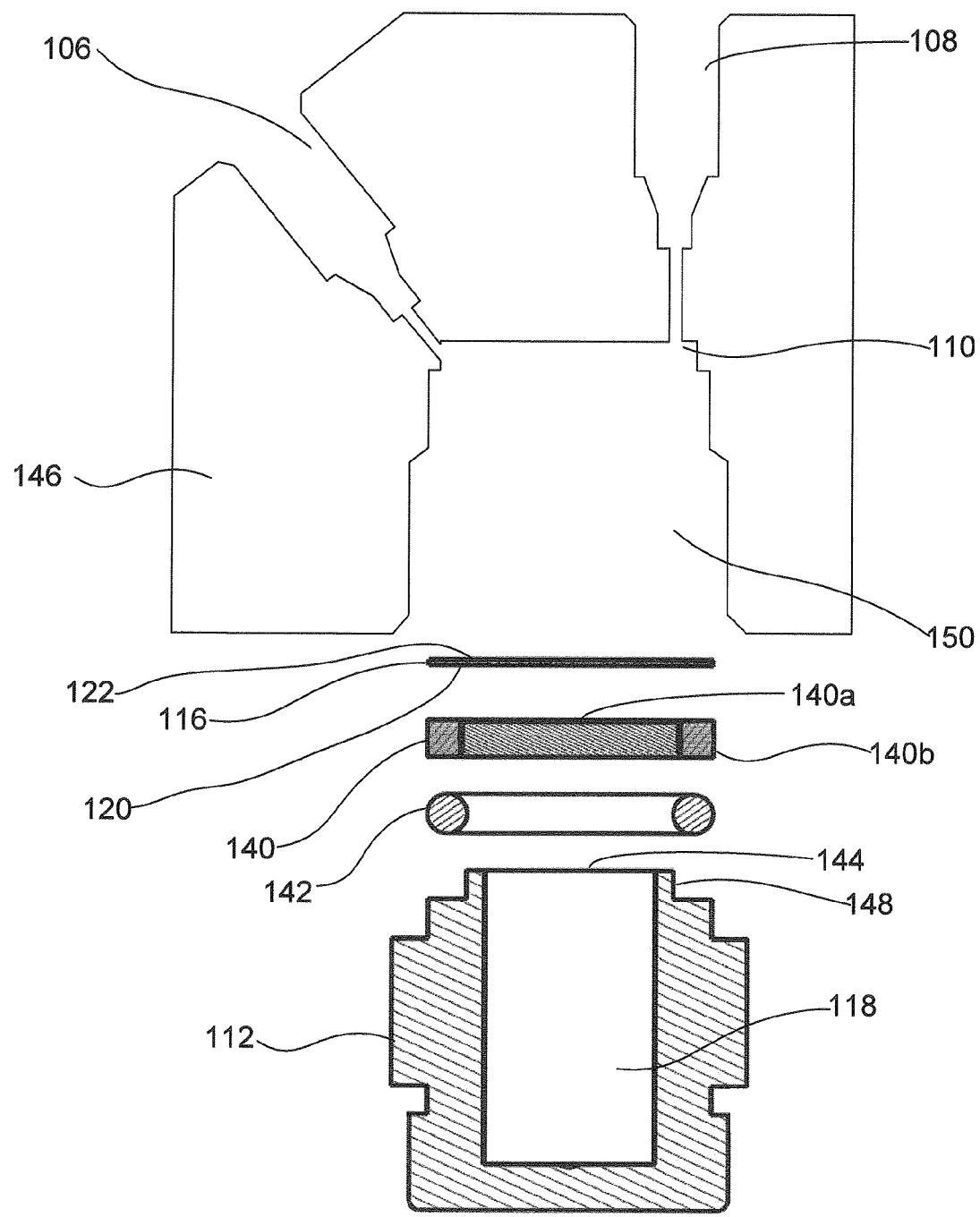
FIG. 2 illustrates an exploded side cross-sectional plan view of the surrogate addition device.

FIG. 2 illustrates an exploded side cross-sectional plan view of the surrogate addition device 102. Surrogate addition device 102 includes a flow chamber block 146, a diffusion barrier 116, a frit 140, an o-ring 142 and a surrogate reservoir 112. Surrogate reservoir 112 can be configured to contain a surrogate solution 118 that includes a surrogate compound. In an embodiment, surrogate reservoir 112 can be in the form of a cylindrical cavity with an open end 144. O-ring 142 can be disposed over an outer cylindrical surface 148. Frit 140 can be optionally disposed over an uppermost surface of surrogate reservoir 112. Where diffusion barrier 116 is not sufficiently rigid, it may require additional support for holding it to surrogate reservoir 112. Frit 140 may be disposed in between an inner surface 120 of diffusion barrier 116 and the uppermost surface of surrogate reservoir 112 for providing support, as illustrated in FIG. 2. Alternatively, frit 140 may be disposed on an outer surface 122 of diffusion barrier 116 (this arrangement is not shown). Frit 140 can include a non-porous washer section 140b and an inner porous section 140a. Non-porous washer section 140b can include a polyetheretherketone or an acetal resin. The acetal resin may be sold under the trademark Delrin®, which may be in the form of a polyoxymethylene, POM (acetal homopolymer). Porous section 140a can include a porous polyethylene or polyetheretherketone material. In addition, frit 140 may be in the form of a screen or mesh material. Diffusion barrier 116 can be disposed over frit 140 so that it substantially covers the one open end 144. Surrogate reservoir 112, o-ring 142, frit 140, and diffusion barrier 116 may all be inserted into a cavity section 150 of flow chamber block 146. Surrogate reservoir 112 may be secured to flow chamber block 146 with a threaded assembly to form a flow chamber 110.

Figure 3:
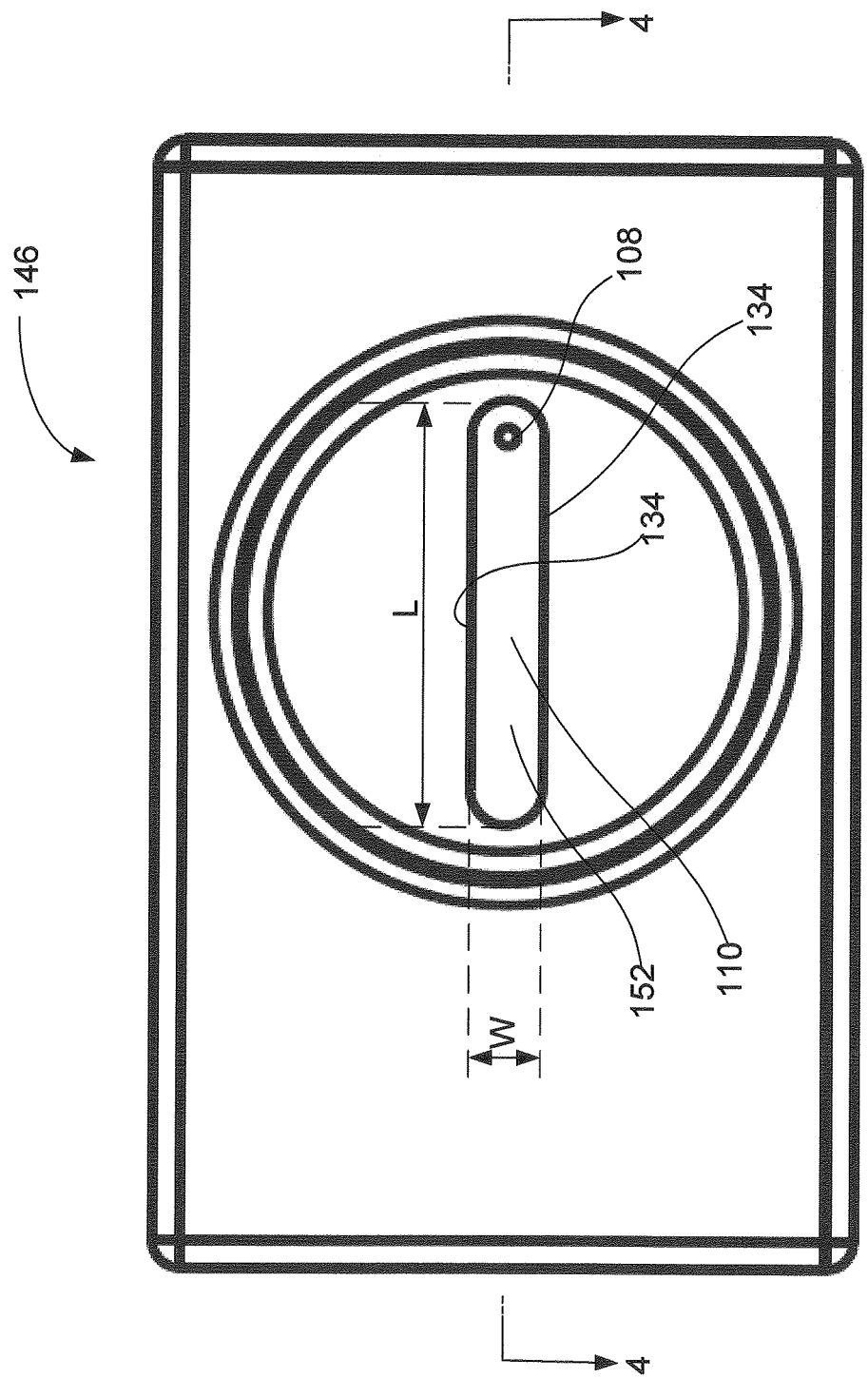
FIG. 3 shows a bottom view of a portion of the surrogate addition device that illustrates a flow chamber.
Figure 4:
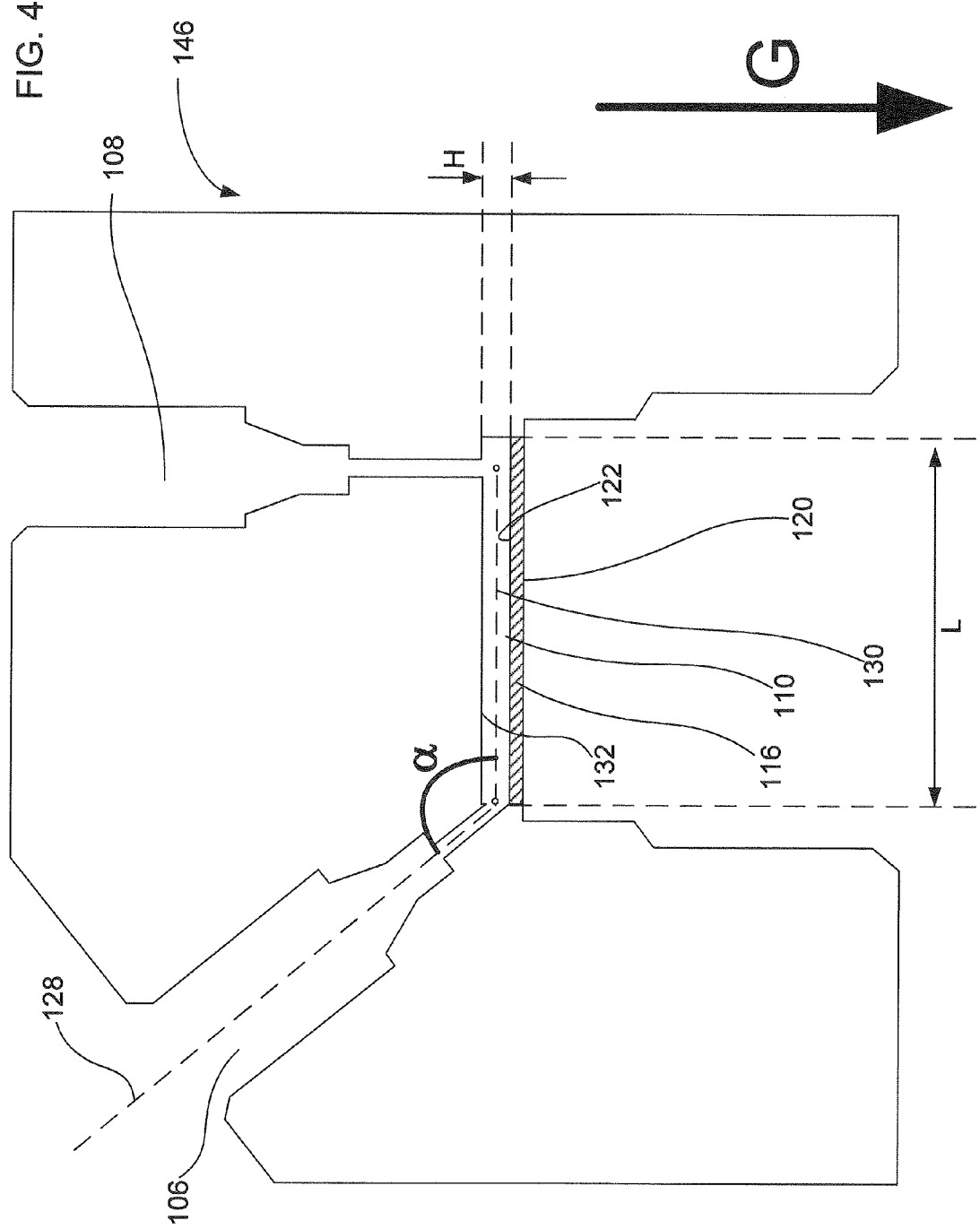
FIG. 4 illustrates a cross-sectional side plan view of a portion of the surrogate addition device with respect to cutting plane line 4, where a diffusion barrier having a planar surface is configured to be approximately perpendicular to a gravity vector line G.
Figure 5:
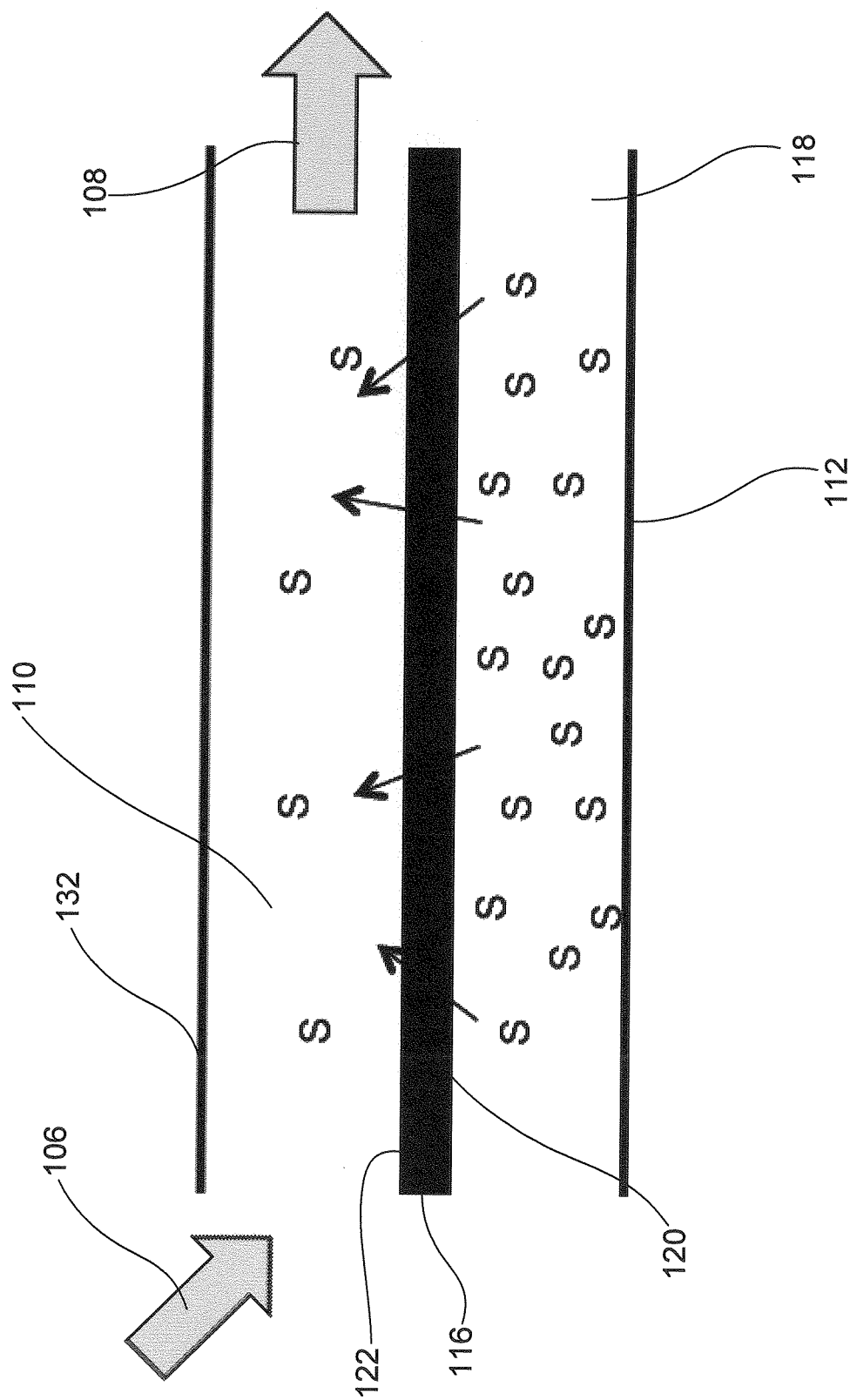
FIG. 5 illustrates a simplified expanded side plan view of the diffusion barrier highlighting the uniform transport of surrogate compound from the surrogate reservoir to the flow chamber.

FIG. 3 shows a bottom view of flow chamber block 146 that illustrates an elliptical groove portion 152 of flow chamber 110. FIG. 4 illustrates a simplified cross-sectional side plan view of flow chamber block 146 and diffusion barrier 116 with respect to cutting plane line 4 of FIG. 3. For the purpose of visual simplicity, frit 140, o-ring 142, and surrogate reservoir 112 are not shown in FIG. 4. Diffusion barrier 116 can include an inner surface 120 and an outer surface 122. Once diffusion barrier is placed into cavity section 150 of flow chamber block 146, inner surface 120 can form a wall of surrogate reservoir 112 to contain the surrogate solution and outer surface 122 can form a wall of flow chamber 110. Flow chamber 110 can be configured to receive a flowing sample solution into an inlet port 106 across outer surface 122 of diffusion barrier 116 and then to an outlet port 108. Diffusion barrier 116 can be configured to diffuse the surrogate compound from surrogate reservoir 112 to flow chamber 110. During a sampling period, an approximately uniform amount of surrogate compound (S) can diffuse across diffusion barrier 116 and into the sample liquid flow, as illustrated in FIG. 5. The sampling period can include a time duration in which the sample solution is pumped through the flow chamber to concentrate the analyte on the solid phase extraction device. The sampling period can be sufficiently long to concentrate analyte to the solid phase extraction device so that it can be tested with an analytical instrument. For example, a sampling period may be about 190 hours or less. In an embodiment, the approximately uniform diffusion rate may have a relative standard deviation of less than about 5% over the sampling period.

Diffusion barrier 116 can be configured so that bulk sample solution essentially does not flow across the barrier during the sampling period. Thus, the diffusion barrier essentially does not allow bulk flow across the barrier, but does allow the surrogate compound (S) to be transported across the barrier. The diffusion rate of the surrogate compound from the surrogate reservoir to the flow chamber may range from about 4 attomoles per minute to about 100 picomoles per minute, preferably range from about 20 femtomoles per minute to about 50 picomoles per minute, and more preferably range from about 100 femtomoles per minute to about 20 picomoles per minute at a flow rate of about one milliliter per minute. The diffusion barrier may have a thickness ranging from about 10 microns to about 500 microns, and preferably ranging from about 40 microns to about 300 microns. The rate of transfer can be controlled by molecular diffusion. The transfer rate can be based on a partial pressure, a concentration gradient, a flow rate, or a combination thereof. The concentration gradient can be a difference between a surrogate compound concentration in the surrogate reservoir and a surrogate compound concentration in the flow chamber. The release rate may be uniform and stable with the condition that the diffusion barrier does not degrade and the pressure, flow rate and/or concentration gradient across the barrier remains approximately constant.

A saturated surrogate solution can be used to create a constant concentration gradient across the diffusion layer. By using a saturated surrogate solution, the surrogate compound concentration remains constant at inner surface 120 in the surrogate reservoir even though a portion of the surrogate compound is transported to flow chamber 110. In addition, the surrogate compound concentration at outer surface 122 may be about zero or a constant value because the surrogate compound is effectively swept out of the flow chamber as it is dosed into the flowing liquid sample solution.

The surrogate compound may be a pesticide, an herbicide, a fertilizer, a pharmaceutical therapeutic, a protein, a derivative thereof, or a combination thereof. An example of a low molecular weight herbicide suitable for use as a surrogate compound may be linuron, which is a methyl urea compound having a molecular weight of 249 grams per mole. Linuron is neutral and hydrophobic compound and may be referred to as 3-(3,4-dichlorophenyl)-1-methoxy-1-methylurea. In an embodiment, a structural analog of the analyte may be used as a surrogate compound. A surrogate compound can be an isotopically labeled compound that can be distinguished from the analyte. In another embodiment, a surrogate solution can include a mixture of isotopically labeled compounds with predetermined ratios. A surrogate compound should be selected that is stable for the duration of the collection and testing time period. In addition, the surrogate compound should be selected so that it is unlikely to be found in an environmental sample by happenstance.

A surrogate compound is a chemical that is added to the sample contemporaneous with the collection process. Ideally, the surrogate compound will have a similar chemical property to the analyte, but still be distinguishable during the analytical measurement. Here, distinguishable refers to a condition where the analytical instrument is capable of measuring analyte and surrogate compound in the sample and that the presence of the surrogate compound does not interfere with the measurement of analyte. A surrogate compound should be selected that has a similar or common property with the analyte so that they both can be reversibly bound to the solid phase extraction device. The similar or common chemical property may refer to the hydrophobicity, hydrophilicity, hydrogen bonding, Van der Waals interactions, dissociation constant, and size of the surrogate compound and the analyte.

When using chromatography to measure the analyte, a surrogate compound may have a different retention time on the column from the analyte based on the affinity to the stationary phase of the column. For liquid chromatography, the surrogate compound and the analyte can have the same chemical property of being soluble in a common solvent system. For gas chromatography, the surrogate and the analyte can have the same chemical property of being volatile at a common temperature range. After the separation step, the surrogate compound and the analyte can have a common chemical property so that they both can be detected using the same detector format. For example, the analyte and surrogate can both be UV-VIS active with extinction coefficients of the same order of magnitude and absorbance wavelengths in the same wavelength region so that the measurement requires a routine detector with the same gain ratios and only one monochromator component. In another example, the analyte and surrogate can both be electrochemically active at a common solvent condition and electrode material so that a coulometric or amperometric detector can be used. In yet another example, the analyte and surrogate can both be conductive in a common solvent so that a conductometric detector can be used.

When using mass spectrometry to measure the analyte, the surrogate compound can have similar chemical properties to the analyte where they both can be ionized using the same ionization technique such as, for example, electrospray ionization. In addition, the surrogate compound and the analyte can have a sufficiently different m/z value that can be easily measured without background interferences.

In an embodiment, the diffusion barrier may be a material such as, for example, a polyether sulfone, a polysulfone, a polyarylether sulfones, a polyvinylidene fluoride, a polypropylene, a polypiperazine amide, a cellulose acetate, or a combination thereof. The diffusion barrier should be inert to the analyte and also the sample liquid. The diffusion barrier may also be in the form of a porous membrane such as those used in microfiltration, ultrafiltration, nanofiltration, reverse osmosis and gas separation. Certain types of porous membranes may be manufactured with a fiber support backing that is integrated with the membrane to provide structural support. It should be noted that the thickness, pore size, and pore tortuosity of diffusion barrier can affect the transport rate of surrogate compound. In an embodiment, the diffusion barrier may be a permselective membrane in the form of a molecular weight cutoff membrane with a molecular weight cutoff range ranging from about 100 grams per mole to about 300 grams per mole where the membrane has a thickness of about 150 microns. Diffusion barrier 116 should not be limited to the above described molecular weight cutoff range because larger pores may be used with thicker membranes and smaller pores may be used with thinner membranes. In an embodiment, diffusion barrier may also be configured to not be charge selective.

Under certain circumstances, the diffusion barrier can be charged with a surfactant that may cause the need to wash the surfactant out before mounting the diffusion barrier to the surrogate addition device. Removal of surfactant can improve the uniformity of the surrogate compound diffusion especially at the initial time intervals. In an embodiment, deionized water can be flowed through the diffusion barrier at about 1 milliliter per minute for about 5 hours to about 24 hours.

Referring back to FIG. 4, flow chamber 110 includes a height H that is defined by outer surface 122 of diffusion barrier 116 and an opposing wall 132 of flow chamber 110. The height H may range from about 0.6 millimeters to about 13 millimeters, and preferably be about 1.2 millimeters. Flow chamber 110 also includes a width W and a length L, as illustrated in FIG. 3. The width W is defined by two side walls 134. The length L is approximately defined by a distance between inlet port 106 and outlet port 108, as shown in FIGS. 3 and 4. The width W and length L may be about 2 millimeters, and about 12 millimeters, respectively. The area of either the inner surface or outer surface of the diffusion barrier may have an approximately rectangular or elliptical shape and may range from about 0.01 $mm^2$ to about 3.5 $mm^2$. In an embodiment, a volume of the flow chamber may be about 25 microliters.

The angled position of inlet port can have an effect on the uniform transport of the surrogate compound to flow chamber 110. Referring back to FIG. 4, an axis 128, running along a direction of a flowing sample solution through inlet port 106, forms an angle $\alpha$ with respect to a line segment 130 running along a direction of a flowing sample solution from inlet port 106 to outlet port 108. In an embodiment, the angle $\alpha$ may range from about 100 degrees to about 170 degrees, preferably range from about 115 degrees to about 145 degrees, and more preferably be about 130 degrees. Surprisingly, the angle $\alpha$ was found to have an effect in providing a uniform transport of surrogate compound during the sampling period.

In an alternative embodiment, the angle $\alpha$ may range from about 10 degrees to about 80 degrees, preferably range from about 25 degrees to about 55 degrees, and more preferably be about 40 degrees. It should be noted that an angle $\alpha$ of about 90 degrees and about 180 degrees may not result in a uniform transport of the surrogate compound to flow chamber 110. This alternative embodiment is slightly more difficult to manufacture than the 100 to 170 degree embodiment because of the angle of drilling an inlet port 106 into flow chamber block 146.

The orientation of the surrogate addition device 102 can also have an effect on the uniform transport of surrogate compound to flow chamber 110. Referring to FIG. 4, the surrogate addition device can have a first position where the outer surface 122 of the diffusion barrier is an approximately planar surface that is approximately perpendicular to a gravity vector line G. Note that the direction of the gravity vector line is parallel to the direction of force caused by gravity towards a center point of earth. In the first position, inlet port 106 and outlet port 108 are both disposed on a top portion of the surrogate addition device, as illustrated in FIG. 4. Referring to FIG. 6, the surrogate addition device can have a second position where the outer surface 122 of the diffusion barrier is an approximately planar surface that is approximately parallel to a gravity vector line. In the second position, inlet port 106 is disposed on a bottom portion of the surrogate addition device and outlet port 108 is disposed on a top portion, as illustrated in FIG. 6. Surprisingly, the second position, where the diffusion barrier is approximately parallel to a gravity vector line, was found to provide a more uniform transport of surrogate compound than the first position. The surrogate addition device can be attached to a bracket or housing so that it can be held in the second position.

It should be noted that surrogate addition device 102 does not require electrical power to add a uniform flux of surrogate compound. Given that the pump may require power for flowing the liquid sample, a non-powered addition of surrogate provides for a more simple system and does not create an additional burden on the energy budget of system 100.

Under certain circumstances, temperature variations may influence the transport of surrogate compound across the diffusion barrier or the binding of surrogate compound and analyte to the solid phase extraction device. As an optional feature, an insulated housing 136 and an insulated line 138 may be used to reduce potential temperature fluctuations. Insulated housing 136 can be configured to contain surrogate addition device 102 and/or the solid phase extraction device 104. Insulated line 138 can be coupled in between sample source 126 and inlet port 106 of flow chamber 110. Insulated line 138 can be made of a material or coated with a material that reduces the rate of heating or cooling caused by the ambient air temperature. The use of insulated line 138 may be implemented where the water source has a temperature different than ambient. For example, lake water collected from a deep portion may be relatively cooler than ambient and thus require an insulated line. Optionally, insulated line 138 may include a heater to elevate the temperature of the sample solution to a constant value.

Once the sample has been pumped through the flow chamber and the surrogate compound has been added, solid phase extraction 104 can be used to bind both the analyte and the surrogate compound. Referring back to FIG. 1, the solid phase extraction device 104 can be fluidically coupled to the outlet port 108 of the flow chamber. Solid phase extraction device 104 can be configured to bind a surrogate compound from the sample solution and output the depleted sample solution to waste container 114. The solid phase extraction can be a form of a container for the analyte and surrogate compound where the bulk of the water has been removed.

In an embodiment, the solid phase extraction device can include a housing that contains a stationary phase. The stationary phase can be configured to bind and hold an analyte and a surrogate. The stationary phase can be in the form of a monolith or a particulate based media. The particulate based media includes inorganic absorptive media and organic polymer media. Examples of inorganic absorptive media include silica, zirconia, titania, and alumina. The stationary phase can be referred to as a selectively sorbent material capable of reversibly binding an analyte and a surrogate compound. Reversibly binding may refer to the retention of the analyte and the surrogate compound from the sample solution and a subsequent unbinding of both analyte and surrogate compound when eluted with an eluent solution. The binding group functionality can be in the form of a reversed phase, normal phase, ion exchange medium, size exclusion, or a combination thereof. Any known retention mechanism can be used to bind the analyte and the surrogate, which includes ionic, hydrophilic, hydrophobic, hydrogen bonding, size, and Van der Waals. At a subsequent step, the analyte and surrogate can be unbound so that they can be measured with an analytical instrument. In an embodiment, the solid phase extraction device can quantitatively remove the analyte and the surrogate compound from sample solution and then completely release them in an appropriate solvent. The solid phase extraction device may also be configured to reversibly bind one or more species of analytes and one or more species of surrogate compounds.

In an embodiment, the solid phase extraction device may include a 40 micron (diameter) macroporous resin grafted with a polyvinylpyrrolidone polymer, which may be commercially available as the InGuard® HRP part number 074034 from Thermo Scientific Dionex.

System 100, as illustrated in FIG. 1, uses only one surrogate addition device. In alternative embodiments, a plurality of surrogate addition devices can be implemented so that the sample source can be monitored with more than one replicate during the same time interval. The replicates can be averaged together to increase accuracy or a difference between replicates can be used to assess the possibility of a system error. In addition, the plurality of surrogate addition devices can also be tested in series where the liquid sample flows across a different surrogate addition device depending on the time interval.

Now that the system for concentrating the analyte with a surrogate addition device has been described, the following will describe a method of using such a system. As a first step, a sample solution from a sample source 126 can be pumped to surrogate addition device 102 using pump 124. A surrogate compound can be added to the sample solution at an approximately uniform transport rate with surrogate addition device 102. The sample solution can be pumped through flow chamber 110 at a flow rate ranging from about 0.5 milliliters per minute to about 2 milliliters per minute. In addition, the sample solution can be pumped through flow chamber 110 at a pressure ranging from about 5 pounds per square inch to about 200 pounds per square inch, and preferably ranging from about 25 pounds per square inch to about 100 pounds per square inch. Next, the sample solution from surrogate addition device 102 can be flowed to solid phase extraction device 104. Solid phase extraction device 104 can bind the analyte and the surrogate compound. The sampling period or collection phase is complete once pump 124 has pumped the sample solution at a uniform flow rate for a predetermined amount of time. Solid phase extraction device 104 may be removed from the system and easily transported to a laboratory.

Figure 7:
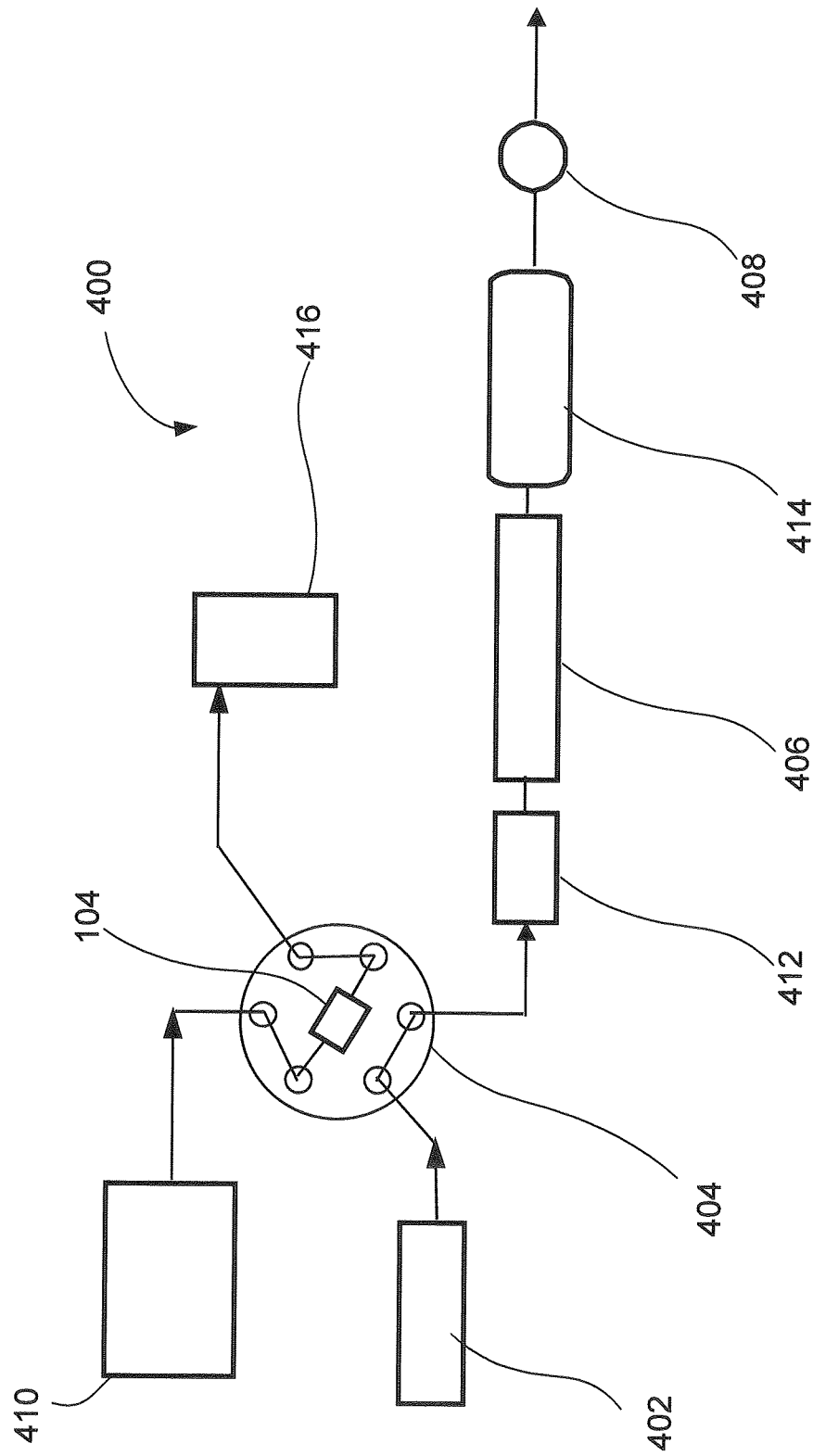
FIG. 7 illustrates a schematic of an on-line system for analyzing an analyte that has been pre-concentrated onto a solid phase extraction device.

At the laboratory, the solid phase extraction device 104 can be attached to an on-line system 400 for analyzing the analyte, as illustrated in FIG. 7. On-line system 400 may include a pump 402, an autosampler 410, a waste container 416, a valve 404, a guard column 412, an analytical column 406, an electrolytic suppressor 414, and a detector 408. After attaching the solid phase extraction device 104, pump 402 can provide an eluent through valve 404 to solid phase extraction device 104. The eluent can be configured to elute (i.e., unbind) the analyte and surrogate compound from the solid phase extraction device. The eluted analyte and surrogate can then be separated on analytical column 406 and analyzed with an analytical instrument. Examples of analytical instruments suitable for use in analyzing the eluted analyte and the eluted surrogate compound may be a mass spectrometer, a gas chromatograph, an ultraviolet-visible spectrometer, a fluorescence spectrometer, an electrochemical detector, a conductometric detector, or a combination thereof.

In an alternative embodiment, the solid phase extraction device can be analyzed off-line where the analyte is eluted into a solvent and collected into a sample bottle. The solvent in the sample bottle can then be injected into an analytical instrument to determine the concentration of analyte.

Example 1

Surrogate addition device 102 was assembled by first pouring a saturated linuron solution into surrogate reservoir 112. A saturated solution of linuron was prepared by adding 0.1 grams of linuron to 600 microliters of water. This surrogate solution was then added into surrogate reservoir 112. Based on the solubility of linuron at 25° C., the surrogate solution has a concentration of about 81 milligrams per liter. O-ring 142 was placed around outer cylindrical surface 148 of surrogate reservoir 112. Next, frit 140 was disposed over surrogate reservoir 112. Frit 140 includes inner porous section 140*a*, which in this case was in the form of porous polyethylene support with a nominal pore size of about 10 microns. A diffusion barrier 116 in the form of a planar flat membrane (TS80, TriSep, Goleta, Calif.) was disposed over frit 140 so that the surrogate solution was in fluidic contact with the membrane. The planar flat membrane had a molecular weight cut off of 150 grams per mole. Cavity section 150 of flow chamber block 146 was disposed over surrogate reservoir 112 and attached together through a threaded arrangement to form and close flow chamber 110.

Figure 8:
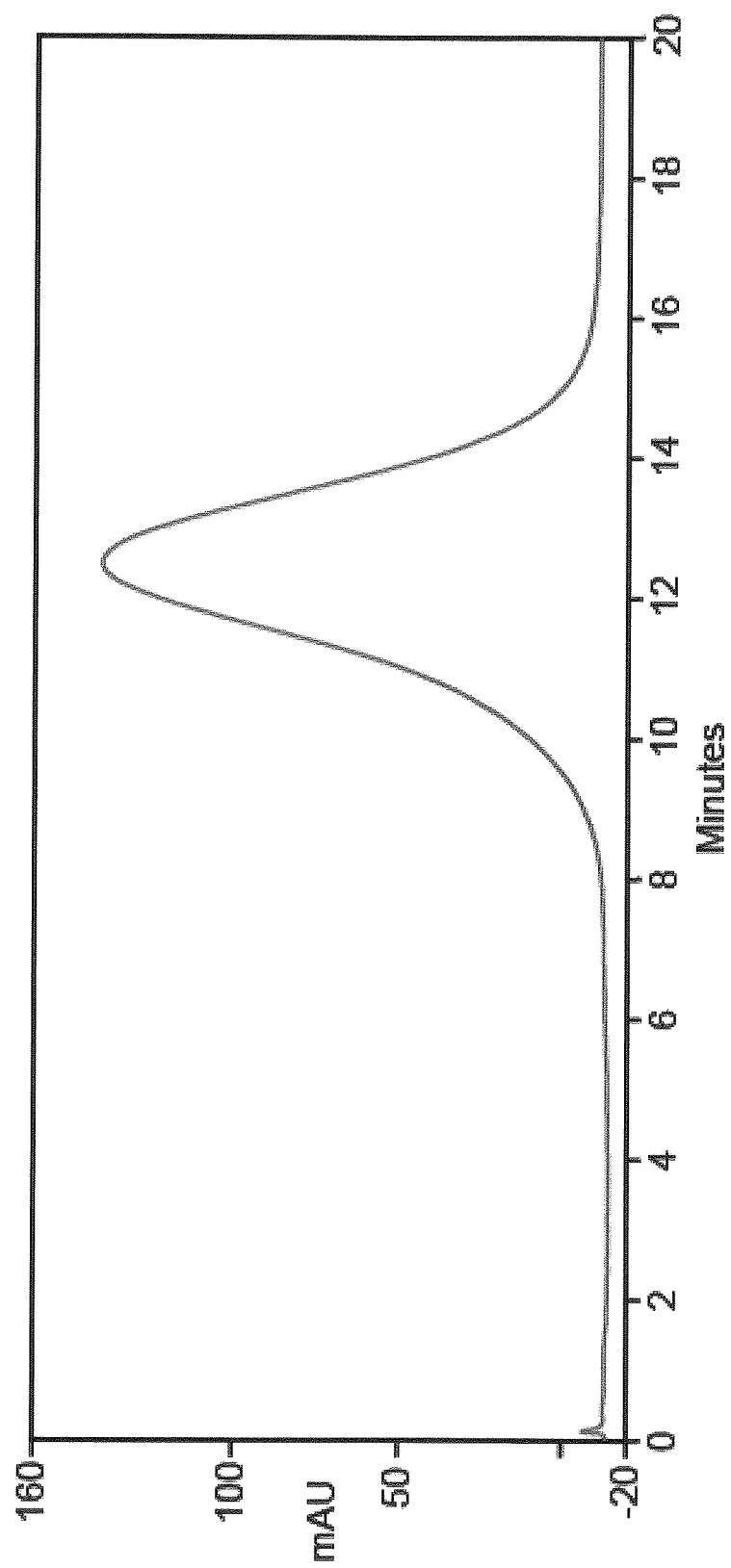
FIG. 8 shows the absorbance units as a function of time where the surrogate compound linuron has been eluted from a solid phase extraction device.

The solid phase extraction device was attached to the surrogate addition device. The solid phase extraction device was a 4.6×50 millimeters column including 40 micron diameter particles of macroporous divinylbenzene resin grafted with polyvinylpyrrolidone. This column generates less than 50 pounds per square inch backpressure when pumping the sample solution at 1 milliliter per minute. The sample solution was flowed through the surrogate addition device and the solid phase extraction device at 1 milliliter per minute for a total time of 8700 minutes. Next, the solid phase extraction device was attached to a HPLC system with a UV detector. An eluent was flowed through the solid phase extraction device where the eluent varied from 30% acetonitrile to 70% acetonitrile in a 20 minute period with a 10 mM acetate buffer at pH 5.4. The eluent flow was in the same direction as the surrogate compound loading step. The eluent flow rate was at about 600 microliters per minute at a temperature of 25° C. Linuron was eluted from the solid phase extraction device and detected with an ultraviolet (UV) detector at 254 nanometers, as is shown in FIG. 8. A peak at about 12 minutes was observed on the chromatogram. The release rate was calculated by dividing the linuron peak area by the volume of sample concentrated on the column.

Example 2

Deionized water was flowed through the surrogate addition device and the solid phase extraction device at a flow rate of 1 milliliter per minute for about 145 hours. The surrogate addition device was orientated in the first position where the planar diffusion barrier was approximately perpendicular to a gravity vector line, in accordance with FIG. 4. The sample flow was periodically stopped so that solid phase extraction device could be tested with a HPLC using a UV detector. Table 1 illustrates the release rate of surrogate compound into the flowing deionized water.

TABLE 1

| Volume | UV response | Time, hour | UV response/ 100 mL |
|---|---|---|---|
| 258.5 | 328.55 | 4.3 | 127.1 |
| 132.4 | 171.08 | 6.5 | 129.2 |
| 951.5 | 1209.69 | 22.4 | 127.1 |
| 142.5 | 176.46 | 24.7 | 123.9 |
| 129.5 | 158.13 | 26.9 | 122.2 |
| 124.6 | 161.91 | 29.0 | 129.9 |
| 92.0 | 120.28 | 30.5 | 130.7 |
| 945.9 | 1249.16 | 46.3 | 132.1 |
| 150.0 | 186.44 | 48.8 | 124.3 |
| 115.0 | 141.55 | 50.7 | 123.1 |
| 1040.9 | 1282.98 | 68.0 | 123.3 |
| 68.0 | 84.28 | 69.2 | 123.9 |
| 109.4 | 133.46 | 71.0 | 122.0 |
| 107.0 | 132.76 | 72.8 | 124.1 |
| 113.5 | 139.01 | 74.7 | 122.5 |
| 1046.8 | 1282.98 | 92.1 | 122.6 |
| 112.0 | 136.67 | 94.0 | 122.0 |
| 113.5 | 136.66 | 95.9 | 120.4 |
| 125.4 | 152.42 | 98.0 | 121.6 |
| 111.4 | 137.26 | 99.8 | 123.3 |
| 950.0 | 1138.37 | 115.7 | 119.8 |
| 105.6 | 129.61 | 117.4 | 122.7 |
| 115.7 | 138.76 | 119.4 | 119.9 |
| 106.7 | 127.01 | 121.1 | 119.0 |
| 124.2 | 148.31 | 123.2 | 119.4 |
| 1313.8 | 1573.16 | 145.1 | 119.7 |

Figure 9:
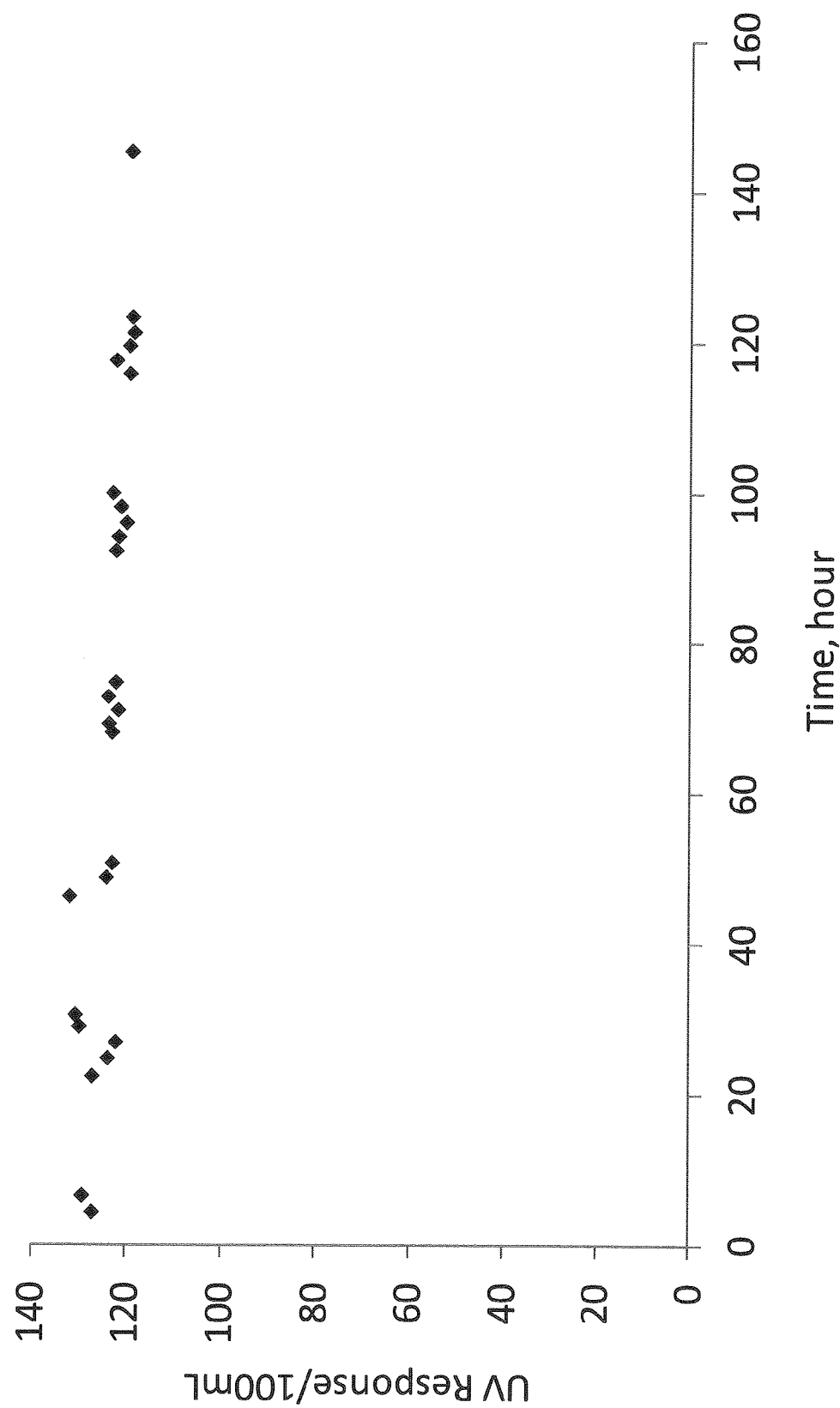
FIG. 9 is a graph showing a UV response, that is proportional to the concentration of a surrogate compound linuron, as a function of time where a planar diffusion barrier is approximately perpendicular to a gravity vector line.

Because the time intervals were not all the same, the UV response was normalized to a 100 milliliter sample volume. Note that the UV response is in units of milliabsorbance unit (mAu)×minutes per volume of deionized water. The milliabsorbance units×minutes represent an area under a curve (see FIG. 8), which is directly proportional to the linuron concentration. Using the data from Table 1, FIG. 9 was generated to show the UV responses as a function of time. A modest decrease in the transport rate of linuron through the membrane was observed was based on a negative slope of is −0.07 mAu/100 mL×hour over the 145 hour period.

Example 3

Figure 6:
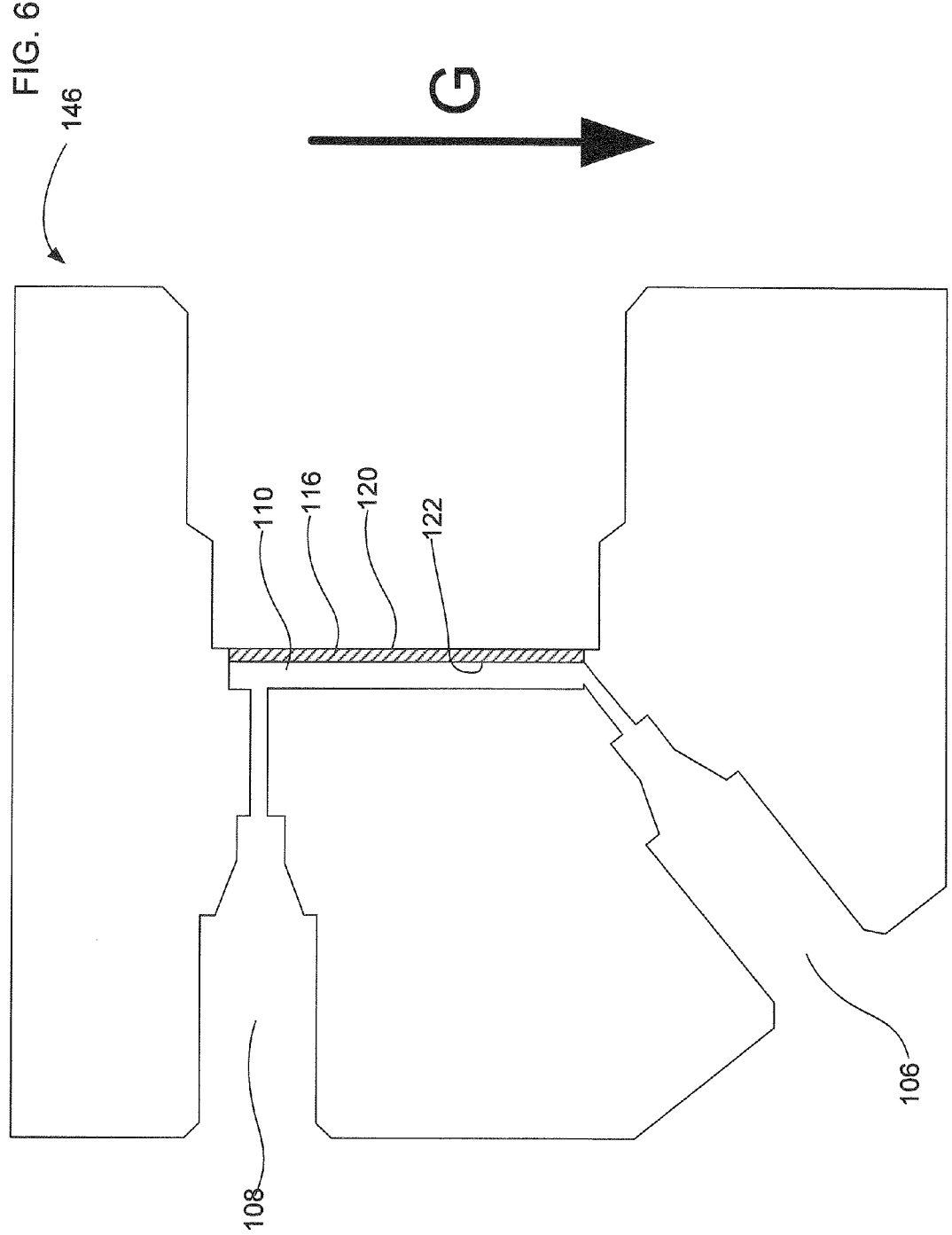
FIG. 6 illustrates a cross-sectional side plan view of a portion of the surrogate addition device where a diffusion barrier having a planar surface is configured to be approximately parallel to a gravity vector line G.

An experiment was performed similar to Example 2 except that the surrogate addition device was orientated in the second position where the planar diffusion barrier was approximately parallel to a gravity vector line, in accordance with FIG. 6. Table 2 illustrates the release rate of surrogate compound into flowing deionized water. For this Example, deionized water was flowed through the surrogate addition device for about 191 hours.

TABLE 2

| Volume, mL | UV response | Time, hour | UV response/ 100 mL |
|---|---|---|---|
| 103.3 | 137.1 | 1.7 | 132.7 |
| 102.4 | 116.1 | 3.4 | 113.4 |
| 96.6 | 109.7 | 5.0 | 113.6 |
| 106.8 | 123.2 | 6.8 | 115.4 |
| 993.0 | 1185.8 | 23.4 | 119.4 |
| 127.4 | 157.7 | 25.5 | 123.8 |
| 100.1 | 124.8 | 27.2 | 124.8 |
| 116.5 | 146.4 | 29.1 | 125.7 |
| 107.8 | 138.1 | 30.9 | 128.1 |
| 995.5 | 1248.5 | 47.5 | 125.4 |
| 128.7 | 153.2 | 49.6 | 119.1 |
| 113.1 | 136.5 | 51.5 | 120.7 |
| 118.0 | 140.6 | 53.5 | 119.2 |
| 101.3 | 123.3 | 55.2 | 121.7 |
| 958.9 | 1201.7 | 71.2 | 125.3 |
| 109.6 | 137.3 | 73.0 | 125.2 |
| 109.3 | 135.3 | 74.8 | 123.8 |
| 103.6 | 131.6 | 76.5 | 127.1 |
| 100.8 | 127.9 | 78.2 | 126.8 |
| 1313.1 | 1654.1 | 100.1 | 126.0 |
| 1339.9 | 1630.3 | 122.4 | 121.7 |
| 1216.8 | 1473.5 | 142.7 | 121.1 |
| 100.8 | 121.3 | 144.4 | 120.4 |
| 148.3 | 182.6 | 146.9 | 123.1 |
| 112.1 | 131.8 | 148.7 | 117.6 |
| 101.9 | 121.5 | 150.4 | 119.3 |
| 928.5 | 1123.3 | 165.9 | 121.0 |
| 104.1 | 123.9 | 167.6 | 119.0 |
| 105.4 | 125.5 | 169.4 | 119.1 |
| 116.0 | 138.7 | 171.3 | 119.6 |
| 101.1 | 119.6 | 173.0 | 118.4 |
| 1080.7 | 1319.5 | 191.0 | 122.1 |
| STDEV | | | 4.3 |
| AVG | | | 121.9 |
| RSD | | | 3.5% |

Figure 10:
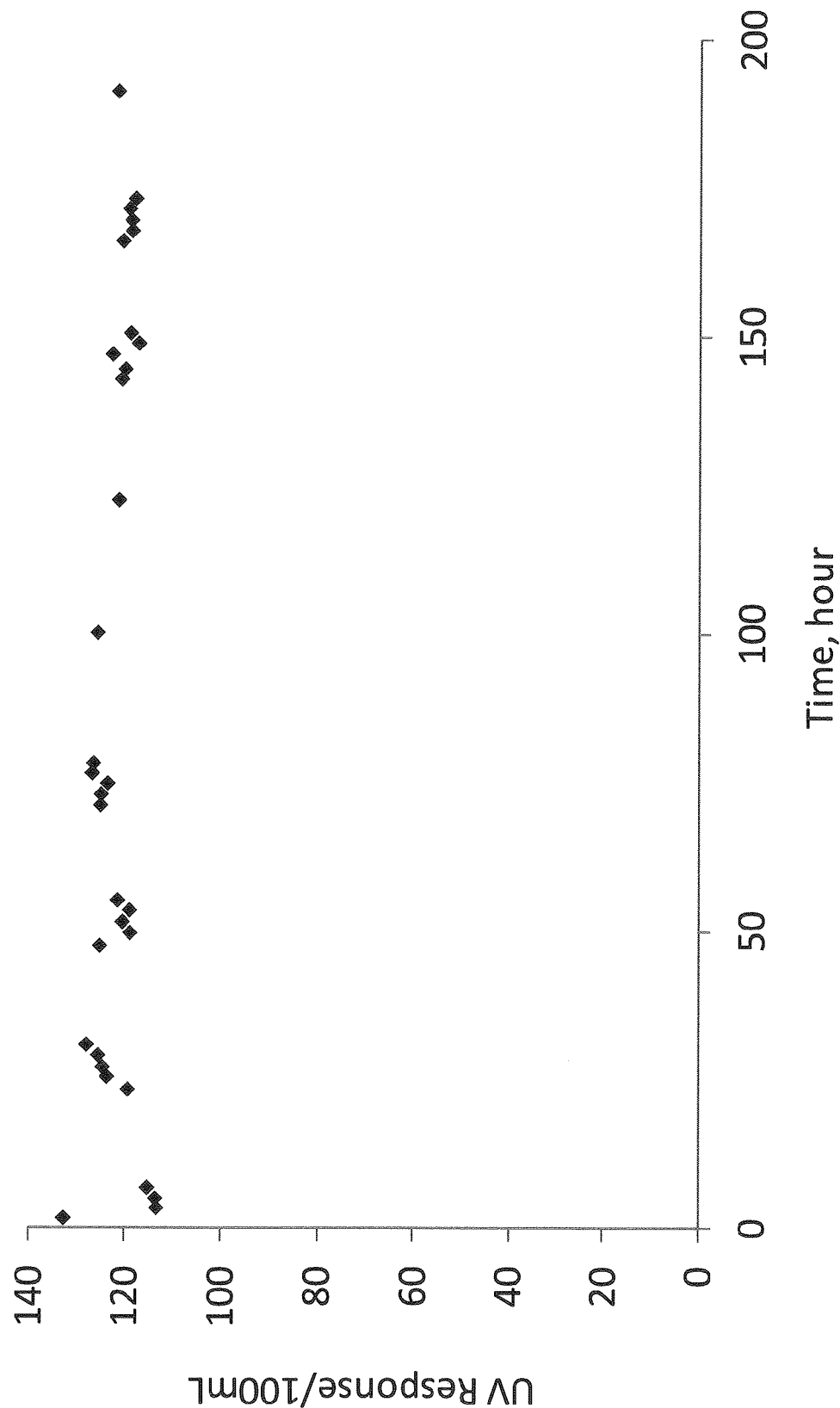
FIG. 10 is a graph showing a UV response, that is proportional to the concentration of a surrogate compound linuron, as a function of time where a planar diffusion barrier is approximately parallel to a gravity vector line.

Using the data from Table 2, FIG. 10 was generated to show the UV responses as a function of time. Table 2 and FIG. 10 show that the transport rate of linuron was approximately uniform over the 191 hour period, which indicated a significant improvement over Example 2. A much smaller decrease in the transport rate of linuron through the membrane was observed with a negative slope of is −0.003 mAu/100 mL×hour over the 191 hour period. Thus, the decrease in transport rate was about 23 times more stable when the planar diffusion barrier was approximately parallel to a gravity vector line as opposed to being approximately perpendicular to the gravity vector line. In addition, the relative standard deviation (RSD) of the linuron transport rate was about 3.5% where the transport rate was sampled at either about 100 milliliters or about 1 liter increments over the sampling period.

Example 4

An experiment was performed similar to Example 3 except that a synthetic drinking water sample solution was flowed through the surrogate addition device. Synthetic drinking water contained 100 milligram per liter chloride, 100 milligram per liter sulfate, 60 milligram per liter bicarbonate, and 12 milligram per liter nitrate, each present as a sodium salt. The surrogate addition device was orientated in the second position where the planar diffusion barrier was approximately parallel to a gravity vector line. Table 3 illustrates the release rate of surrogate compound into the flowing synthetic drinking water. For this Example, synthetic drinking water was flowed through the surrogate addition device for about 141 hours.

TABLE 3

| volume | UV response | Time, hour | UV response/ 100 mL |
|---|---|---|---|
| 97.3 | 110.22 | 1.6 | 113.3 |
| 106.9 | 121.61 | 3.4 | 113.8 |
| 978.6 | 1130.1 | 19.7 | 115.5 |
| 156.0 | 167.11 | 22.3 | 107.1 |
| 102.8 | 109.41 | 24.0 | 106.4 |
| 121.1 | 127.9 | 26.0 | 105.6 |
| 966.3 | 1038.87 | 42.1 | 107.5 |
| 101.4 | 111.22 | 43.8 | 109.7 |
| 111.7 | 124.28 | 45.7 | 111.3 |
| 103.5 | 117.29 | 47.4 | 113.3 |
| 110.4 | 125.63 | 49.3 | 113.8 |
| 1005.4 | 1130.63 | 66.0 | 112.5 |
| 102.0 | 111.41 | 67.7 | 109.2 |
| 134.2 | 154.24 | 70.0 | 115.0 |
| 105.2 | 116.92 | 71.7 | 111.1 |
| 116.9 | 137.94 | 73.7 | 118.0 |
| 1161.2 | 1345.26 | 93.0 | 115.9 |
| 1535.1 | 1718.46 | 118.6 | 111.9 |
| 1131.8 | 1281.41 | 137.5 | 113.2 |
| 102.9 | 117.18 | 139.2 | 113.8 |
| 103.3 | 115.22 | 140.9 | 111.5 |

Figure 11:
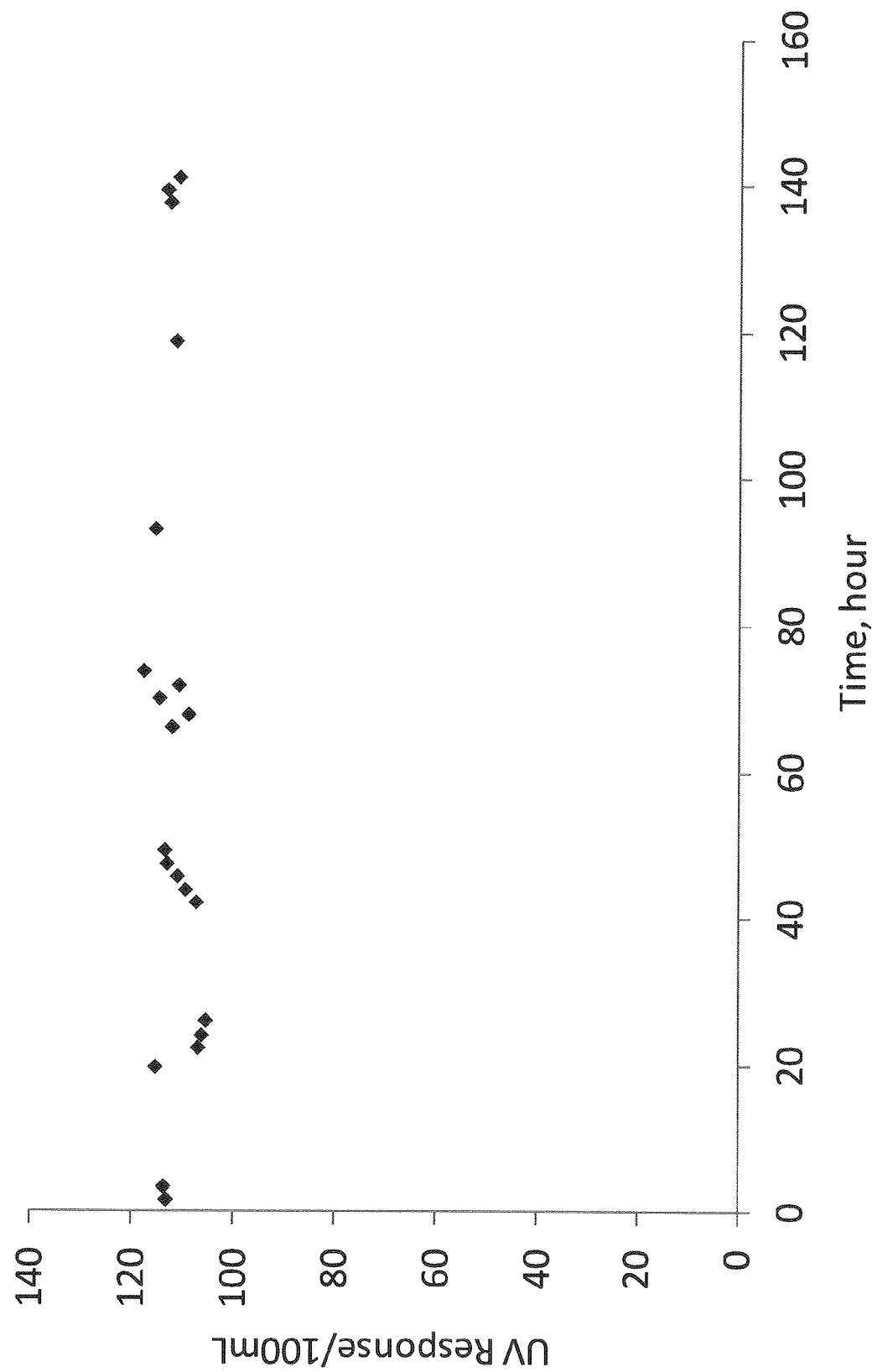
FIG. 11 is a graph showing a UV response, that is proportional to the concentration of a surrogate compound linuron, as a function of time where the liquid stream is a synthetic drinking water.

Using the data from Table 3, FIG. 11 was generated to show the UV responses as a function of time. Similar to FIG. 10, FIG. 11 shows that the transport rate of linuron was uniform and does not decrease over the 141 hour period. Thus, in addition to deionized water, the surrogate addition device also provides a uniform transport rate when using synthetic drinking water.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A system for concentrating an analyte from a sample source comprising:
  (a) a pump configured to pump a sample solution from the sample source to a solid phase extraction device;
  (b) a surrogate addition device that is fluidically coupled to an outlet of the pump, the surrogate addition device comprising:
    (i) a surrogate reservoir configured to contain a surrogate solution where the surrogate solution includes a surrogate compound;
    (ii) a flow chamber including an inlet port and an outlet port; and
    (iii) a diffusion barrier in which at least a portion of the diffusion barrier is disposed in between the surrogate reservoir and the flow chamber, the diffusion barrier including an inner surface and an outer surface, the inner surface forming a wall of the surrogate reservoir, the outer surface forming a wall of the flow chamber, the flow chamber being configured to receive a flowing sample solution across the outer surface of the diffusion barrier from the pump, the diffusion barrier being configured to diffuse the surrogate compound from the surrogate reservoir to the flow chamber; and
  (c) the solid phase extraction device is fluidically coupled to the outlet port of the flow chamber, the solid phase extraction device being configured to bind the surrogate compound and the analyte from the sample solution,
  in which an axis, running along a direction of flowing sample solution through the inlet port, forms an angle with respect to a line segment running along a direction of a flowing sample solution from the inlet port to the outlet port, the angle ranging from about 100 degrees to about 170 degrees.

2. The system of claim 1, in which the diffusion barrier is also configured to have an approximately uniform diffusion rate of the surrogate compound to the flow chamber during a sampling period, the sampling period comprising a time duration in which the sample solution is pumped through the flow chamber to concentrate the analyte on the solid phase extraction device.

3. The system of claim 2, in which the approximately uniform diffusion rate has a relative standard deviation of less than about 5%.

4. The system of claim 1, in which there is essentially no bulk flow of sample solution across the diffusion barrier during a sampling period, the sampling period comprising a time duration in which the sample solution is pumped through the flow chamber to concentrate the analyte on the solid phase extraction device.

5. The system of claim 1, in which the surrogate addition device further comprises a frit configured to retain the diffusion barrier to the surrogate reservoir.

6. The system of claim 1, in which the diffusion barrier is configured to have a diffusion rate of the surrogate compound from the surrogate reservoir to the flow chamber ranging from about 4 attomoles per minute to about 100 picomoles per minute.

7. The system of claim 1, in which the outer surface of the diffusion barrier is an approximately planar surface, the diffusion barrier being configured with the planar surface approximately parallel to a gravity vector line.

8. The system of claim 1, in which the surrogate reservoir contains the surrogate compound and the surrogate compound is selected from the group consisting of a pesticide, an herbicide, a fertilizer, a pharmaceutical therapeutic, and a combination thereof.

9. The system of claim 1, in which the diffusion barrier is a material selected from the group consisting of a polyether sulfone, a polysulfone, a polyarylether sulfones, a polyvinylidene fluoride, a polypropylene, a polypiperazine amide, a cellulose acetate, and a combination thereof.

10. The system of claim 1, in which the diffusion barrier comprises a molecular weight cutoff membrane having a molecular weight cutoff range ranging from about 100 grams per mole to about 300 grams per mole.

11. The system of claim 1, in which the solid phase extraction device comprises a selectively sorbent material configured to retain the analyte and the surrogate compound from the sample solution and also to release the analyte and the surrogate compound upon elution with an eluent.

12. A surrogate addition device comprising:
    (a) a surrogate reservoir configured to contain a surrogate solution where the surrogate solution includes a surrogate compound;
    (b) a flow chamber including an inlet port and an outlet port; and
    (c) a diffusion barrier in which at least a portion of the diffusion barrier is disposed in between the surrogate reservoir and the flow chamber, the diffusion barrier including an inner surface and an outer surface, the inner surface forming a wall of the surrogate reservoir, the outer surface forming a wall of the flow chamber, the flow chamber being configured to receive a flowing sample solution across the outer surface of the diffusion barrier, the diffusion barrier being configured to diffuse the surrogate compound from the surrogate reservoir to the flow chamber, in which an axis, running along a direction of a flowing sample solution through the inlet port, forms an angle with respect to a line segment running along a direction of a flowing sample solution from the inlet port to the outlet port, the angle ranging from about 100 degrees to about 170 degrees.

13. The surrogate addition device of claim 12, in which the diffusion barrier is also configured to have an approximately uniform diffusion rate of the surrogate compound to the flow chamber during a sampling period, the sampling period comprising a time duration in which the sample solution is pumped through the flow chamber to concentrate the analyte on the solid phase extraction device.

14. The surrogate addition device of claim 13, in which the approximately uniform diffusion rate has a relative standard deviation of less than about 5%.

15. The surrogate addition device of claim 12, in which there is essentially no bulk flow of the sample solution across the diffusion barrier during a sampling period, the sampling period comprising a time duration in which the sample solution is pumped through the flow chamber to concentrate the analyte on the solid phase extraction device.

16. The surrogate addition device of claim 12, in which the surrogate addition device further comprises a frit configured to retain the diffusion barrier to the surrogate reservoir.

17. The surrogate addition device of claim 12, in which the diffusion barrier is configured to have a diffusion rate of the surrogate compound from the surrogate reservoir to the flow chamber ranging from about 4 attomoles per minute to about 100 picomoles per minute.

18. The surrogate addition device of claim 12, in which the outer surface of the diffusion barrier is an approximately planar surface, the diffusion barrier being configured with the planar surface approximately parallel to a gravity vector line.

19. The surrogate addition device of claim 12, in which the surrogate reservoir contains the surrogate compound and the surrogate compound is selected from the group consisting of a pesticide, an herbicide, a fertilizer, a pharmaceutical therapeutic, and a combination thereof.

20. The surrogate addition device of claim 12, in which the diffusion barrier is a material selected from the group consisting of a polyether sulfone, a polysulfone, a polyarylether sulfones, a polyvinylidene fluoride, a polypropylene, a polypiperazine amide, a cellulose acetate, and a combination thereof.

21. The surrogate addition device of claim 12, in which the diffusion barrier comprises a molecular weight cutoff membrane having a molecular weight cutoff range ranging from about 100 grams per mole to about 300 grams per mole.

22. The surrogate addition device of claim 12, in which the flow chamber includes a height that is defined by the outer surface of the diffusion barrier and an opposing wall of the flow chamber, the height ranging from about 0.6 to about 13 millimeters.

* * * * *